US00PP23344P3

(12) United States Plant Patent
Suphachadiwong

(10) Patent No.: US PP23,344 P3
(45) Date of Patent: Jan. 22, 2013

(54) *VANDA* PLANT NAMED 'SPCDW0901'

(50) Latin Name: *Vanda* hybrid
Varietal Denomination: SPCDW0901

(75) Inventor: Thumrong Suphachadiwong, Chonburi (TH)

(73) Assignee: Suphachatwong (TH)

( * ) Notice: Subject to any disclaimer, the term of this patent is extended or adjusted under 35 U.S.C. 154(b) by 281 days.

(21) Appl. No.: 12/661,938

(22) Filed: Mar. 24, 2010

(65) Prior Publication Data

US 2011/0239338 P1 Sep. 29, 2011

(51) Int. Cl.
*A01H 5/00* (2006.01)

(52) U.S. Cl. ..... Plt./311

(58) Field of Classification Search ..... Plt./311
See application file for complete search history.

(56) References Cited

OTHER PUBLICATIONS

UPOV ROM GTITM Computer Database, GTI Jouve Retrieval Software 2011/03 Citation for 'SPCDW0901'.*

* cited by examiner

*Primary Examiner* — Wendy C Haas

(57) ABSTRACT

A new and distinct *Vanda* hybrid cultivar named 'SPCDW0901' is disclosed, characterized by unique purple coloration of the petals and overall, compact plant habit and unusual low temperature tolerance. The new variety is a *Vanda*, and is normally used as an ornamental plant.

1 Drawing Sheet

Latin name of the genus and species: *Vanda* hybrid.
Variety denomination: 'SPCDW0901'.

BACKGROUND OF THE INVENTION

The new cultivar was discovered as a chance, naturally occurring mutation of the unpatented commercial variety *Vanda* hybrid 'Blue Magic.' The inventor, Mr. Thumrong Suphachadiwong, a citizen of Thailand, discovered the new variety as a chance mutation among several hundred plants produced at a commercial laboratory in Chonburi, Thailand. The new variety was discovered in May 2003 by the inventor.

Asexual reproduction of the new cultivar 'SPCDW0901' by meristem tissue culture was performed at a commercial laboratory in Chonburi, Thailand later in 2003. Since that time, multiple generations have been reproduced, and have shown that the unique features of this cultivar are stable and reproduced true to type through successive generations.

SUMMARY OF THE INVENTION

The cultivar 'SPCDW0901' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SPCDW0901.' These characteristics in combination distinguish 'SPCDW0901' as a new and distinct *Vanda* hybrid cultivar:

1. Compact overall plant
2. Unique purple and white flower coloration
3. Unusually good tolerance for colder temperatures

PARENT COMPARISON

Plants of the new cultivar 'SPCDW0901' are similar to plants of the parent variety unpatented *Vanda* hybrid 'Blue Magic' in most horticultural characteristics. However, plants of the new cultivar 'SPCDW0901' produce purple and white colored flowers compared to the blue and white flowers of Blue Magic.

COMMERCIAL COMPARISON

Plants of the new cultivar 'SPCDW0901' are similar to plants of the unpatented commercial variety, *Vanda* hybrid 'Pink Magic' in most horticultural characteristics. However, plants of the new cultivar 'SPCDW0901' produce purple and white flowers, whereas 'Pink Magic' produces pink and white colored flowers.

Plants of the new cultivar 'SPCDW0901' are similar to plants of the commercial variety, *Vanda* hybrid 'SPCDW0902' in most horticultural characteristics. However, plants of the new cultivar 'SPCDW0901' produce purple and white flowers, whereas 'SPCDW0902' produces white flowers. Additionally plants 'SPCDW0901' are taller and wider than plants of 'SPCDW0902'.

BRIEF DESCRIPTION OF THE PHOTOGRAPH

The accompanying photograph in FIG. 1 illustrates in full color a typical plant of 'SPCDW0901' grown in a greenhouse. The pot size is a commercial 11 cm container. The plant shown is approximately 5 years old. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001 except where general terms of ordinary dictionary significance are used. The following observations and measurements describe 'SPCDW0901' plants grown in a commercial greenhouse in Honselersdijk, the Netherlands. Temperature ranged from 23° C. during the day and 19° C. at night. Light levels were at a minimum of 10,000 lux, including supplemental lighting given during naturally dark periods. During the naturally darkest days supplemental lighting of 10,000 lux was given for 16 hours per day. Measurements and numerical values represent averages of typical flowering types. No chemical or photoperiodic treatments were given.

Botanical classification: *Vanda* hybrid 'SPCDW0901'.

PROPAGATION

Type of propagation typically used: Tissue culture.

General propagation: The time needed from the start of a mericlone to get the small plants ready for deflasking is approximately 24 months under a controlled temperature of about 26 degrees Celsius. After that period they have matured roots. Young tissue culture plantlets start to make roots after approximately 18 months in flasks.

Root description: Moderately to heavy rooting with aerial roots only. Roots very fleshy, non-fibrous. Average length of old roots: 37.9 cm, average diameter of old roots: 2 mm. Average length of young roots: 28.9, average diameter of young roots: 7 mm. Old roots colored near RHS Yellow-Green 147C. Young roots colored near RHS Greyed-Green 192D.

PLANT

Growth habit: Monopodial, upright.

Height from foliage base to top of foliage: Average height from base (plant grown in hanging basket, so no soil line present) to top of foliage: 37.9 cm.

Height from foliage base to top of flowers: Average height from base (plant grown in hanging basket, so no soil line present) to top of foliage: 67.5 cm.

Plant spread: Average: 45.7 cm at widest, 30.1 cm at narrowest.

Normal pot size: Hanging basket (8×8 cm square) or 11 cm.

Growth rate: Moderate.

Number of leaves per plant: Average: 28.

FOLIAGE

Leaf:

*Arrangement*.—Distichous.

*Average length*.—Approximately 19.4 cm.

*Average width*.—Approximately 2.9 cm.

*Shape of blade*.—Ligulate, carinate, moderately twisted lengthways.

*Aspect*.—Very slightly curved.

*Apex*.—Unequal praemorse.

*Base*.—Sheathing. Sheath length: Average 2.4 cm. Sheath width: Average 1.6 cm. Sheath color: Near RHS Yellow-Green 144C.

*Margin*.—Entire.

*Texture of top surface*.—Smooth, dull.

*Texture of bottom surface*.—Smooth, dull.

*Color*.—Young foliage upper side: Near RHS Yellow-Green 146B. Young foliage under side: In between RHS Yelow-Green 144A and Yelow-Green 146B. Mature foliage upper side: Near RHS Yellow-Green 146B. Mature foliage under side: Near RHS 146B.

*Venation*.—Type: Parallel. Venation coloration: RHS Yellow-Green 146B.

Petiole: No petioles present, leaves sessile.

FLOWERING CHARACTERISTICS

General description:

*Flower bud*.—Rate of opening: Approximately 5 days before opening. Length: Approximately 1.9 cm. Diameter: Approximately 1.6 cm. Shape: Broad ovate, spur pointing upward. Color: Near RHS Purple-Violet N80C, veined darker; RHS Purple-Violet N80B, spur lighter; near RHS Purple 77D, base near RHS Yellow-Green 145C.

*Peduncle*.—Length: Approximately 42.8 cm. Width: Approximately 0.6 cm. Aspect: Approximately 40° angle to rosette. Strength: Strong. Texture: Smooth, moderately glossy. Color: Between RHS Yellow-Green 143A and Yellow-Green 144A.

Inflorescence:

*Flowers per stem*.—Average: 8.

*Inflorescence arrangement*.—Axially placed raceme.

*Inflorescence height*.—Approximately 24.6 cm.

*Inflorescence width*.—Approximately 20.4 cm.

Individual flowers:

*Flower type*.—Zygomorphic (orchidaceous), typical shape for the genus *Vanda*.

*Shape*.—Zygomorphic, consisting of three sepals and three petals, one of which is transformed into a labellum (lip).

*Length*.—Approximately 10.8 cm.

*Width*.—Approximately 10.7 cm.

*Depth*.—Approximately 3.8 cm.

*Fragrance*.—No fragrance.

*Persistent*.—No.

*Quantity of petals*.—3 — (2 regular petals and a labellum (lip), described separately).

Petals:

*Arrangement*.—One lateral petal on each side.

*Length*.—Approximately 5.5 cm.

*Width*.—Approximately 4.5 cm.

*Shape*.—Ovate.

*Apex*.—Obtuse.

*Base*.—Cuneate.

*Margin*.—Entire.

*Texture*.—Upper forward surface: Smooth, dull.

*Texture*.—Lower back surface: Smooth, dull.

*Color*.—Most of the flower color is made up of the heavily colored venation. The surface color given below is the actual petal color. The purple coloration, which is most prominent is described in Venation color. When opening, forward surface: Between RHS Red 54D and White N155A. When opening, back surface: Between RHS Red 54D and White N155A. Fully Opened, forward surface: Near RHS Purple-Violet N80B. Fully Opened, back surface: Near RHS Purple-Violet N80B. Fading, forward surface: Not fading. Fading, back surface: Not fading. Color Venation Fully Opened, forward surface: Near RHS Purple N78B near the margin, Purple N78A. Color Venation Fully Opened, back surface: Near RHS Purple N78B near the margin, Purple N78A.

Labellum/lip:

*Shape*.—Three-lobed, lateral lobes involute, central lobe bi-lobed, with revolute margins.

*Length*.—Approximately 2.0 cm.
*Width*.—Approximately 1.4 cm.
*Texture*.—Smooth, dull, with 3 callosities.
*Tip*.—Bi-lobed.
*Base*.—Cuneate.
*Color*.—When opening, forward surface: Lateral lobes Red-Purple 70B with reticulation near White N155A small central blotch Near Yellow 13B; central lobe (including callosities) Purple N78A, base of central lobe White N155A. When opening, back surface: Lateral lobes near RHS Purple 75A with reticulation near White N155A; central lobe near Purple 77B, base of central lobe near White N155A. Fully Opened, forward surface: Lateral lobes near Red-Purple 70B with reticulation near White N155A small central blotch near Yellow 13A; central lobe (including callosities) Near Purple N78A, base of central lobe near White N155A. Fully Opened, back surface: Lateral lobes near Purple 75A with Purple 76D reticulation; central lobe near Purple 77B, base of central lobe near White N155A. Fading, forward surface: Not fading. Fading, back surface: Not fading. Color Venation Fully Opened, forward surface: No venation visible on labellum. Color Venation Fully Opened, back surface: No venation visible on labellum.
*Margin*.—Entire.

Spurs:
*Quantity*.—Average: 1.
*Appearance*.—Short triangular, in line with central lobe of labellum.
*Length*.—Approximately 1.0 cm.
*Width*.—Approximately 0.3 cm.
*Height*.—Approximately 0.6 cm.
*Shape*.—Short triangular.
*Apex*.—Obtuse.
*Base*.—Broad cuneate.
*Margin*.—Entire.
*Texture*.—Smooth, slightly glossy.
*Color*.—Near RHS Purple 76B.

Sepals:
*Quantity*.—Average: 3.
*Appearance*.—One dorsal sepal (pointing upright) and two lateral sepals.
*Length*.—Approximately 5.9 cm.
*Width*.—Dorsal sepal approximately 4.8 cm. Lateral sepals approximately 5.7 cm.
*Shape*.—Broad ovate.
*Apex*.—Obtuse.
*Base*.—Cuneate.
*Margin*.—Entire.
*Texture*.—Smooth, dull.
*Color*.—Near RHS White N155A with blush near Purple-Violet N80B strongly veined near Purple N78B, near the margin near Purple N78A.

Pedicels:
*Length*.—Approximately 6.5 cm.
*Diameter*.—Approximately 0.5 cm.
*Angle*.—Approximately 45° angle to peduncle.
*Strength*.—Very strong.
*Texture*.—Smooth, axially angled with 5 "ribs", axially twisted (due to resupination), moderately glossy.
*Color*.—Near RHS Purple 76D, base near Yellow-Green 146C.

REPRODUCTIVE ORGANS

Stamens, style and stigma fused into column: Yes.
*Column length*.—Approximately 0.5 cm.
*Column diameter*.—Approximately 0.7 cm.
*Column color*.—Near RHS White N155C.

Ovary:
*Position*.—Inferior.
*Diameter*.—Approximately 0.5 cm.
*Color*.—Near RHS Purple 76D.

Pollinia color: Near RHS Yellow 17B.

OTHER CHARACTERISTICS

Disease resistance: Neither resistance nor susceptibility to normal diseases and pests of *Vanda* have been obvserved.

Drought tolerance and cold tolerance: Unusually low temperature tolerance to a minimum 6 degrees Celsius.

Fruit/seed production: Not observed to date.

What is claimed is:

1. A new and distinct cultivar of *Vanda* plant named 'SPCDW0901' as herein illustrated and described.

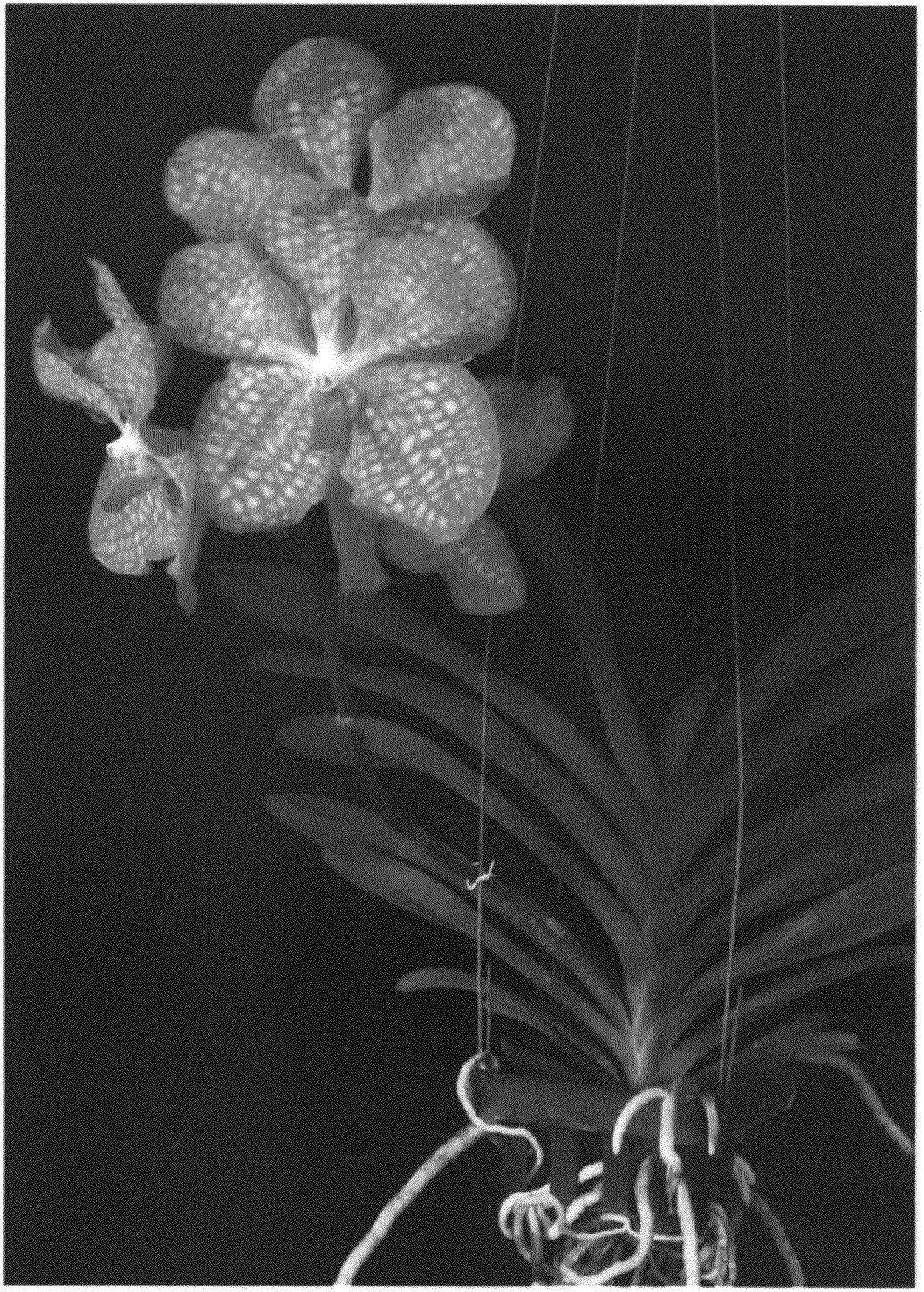

* * * * *